United States Patent
Bleckmann et al.

(10) Patent No.: US 6,821,934 B1
(45) Date of Patent: Nov. 23, 2004

(54) FLOWABLE PREPARATIONS OF THE WATER-IN-OIL EMULSION TYPE HAVING AN INCREASED WATER CONTENT

(75) Inventors: Andreas Bleckmann, Ahrensburg (DE); Rainer Kröpke, Schenefeld (DE); Günther Schneider, Hamburg (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/719,670

(22) PCT Filed: Jun. 16, 1999

(86) PCT No.: PCT/EP99/05816

§ 371 (c)(1),
(2), (4) Date: Dec. 14, 2000

(87) PCT Pub. No.: WO99/65599

PCT Pub. Date: Dec. 23, 1999

(30) Foreign Application Priority Data

Jun. 18, 1998 (DE) .......................................... 198 27 184
Nov. 25, 1998 (DE) .......................................... 198 54 497

(51) Int. Cl.[7] .......................... A61K 7/075; A61K 7/50; B01F 17/34; C11D 1/74
(52) U.S. Cl. .......................... 510/119; 424/59; 424/60; 510/130; 510/136; 510/417; 514/845; 514/846; 514/943; 516/29; 516/30
(58) Field of Search ..................... 516/29, 30; 510/136, 510/417, 119, 130; 514/845, 846, 943

(56) References Cited

U.S. PATENT DOCUMENTS

| | | | | |
|---|---|---|---|---|
| 3,117,929 A | * | 1/1964 | McCoy et al. ............. | 516/29 X |
| 4,115,314 A | * | 9/1978 | Oppenlaender et al. ....... | 516/30 |
| 4,384,974 A | * | 5/1983 | Guthauser ................. | 516/29 X |
| 4,446,044 A | * | 5/1984 | Rutkiewic et al. ......... | 516/30 X |
| 5,308,526 A | * | 5/1994 | Dias et al. ............... | 510/417 X |
| 5,597,792 A | * | 1/1997 | Klier et al. .................. | 510/417 |
| 5,639,797 A | * | 6/1997 | Kropke et al. .......... | 514/846 X |
| 5,851,978 A | * | 12/1998 | Shana'a ................... | 510/136 X |
| 5,863,461 A | * | 1/1999 | Ansmann et al. ............. | 516/29 |
| 5,939,375 A | * | 8/1999 | Müller et al. ................ | 510/417 |
| 2002/0146438 A1 | * | 10/2002 | Bleckman et al. .......... | 424/401 |

FOREIGN PATENT DOCUMENTS

| WO | WO 98/17232 | 4/1998 |
|---|---|---|
| WO | Wo 98/17238 | 4/1998 |

* cited by examiner

*Primary Examiner*—Daniel S. Metzmaier
(74) *Attorney, Agent, or Firm*—Norris McLaughlin & Marcus PA

(57) ABSTRACT

Water-in-oil emulsions
(a) with a viscosity of at most 5000 mPa.s
(b) with a content of water and water-soluble substances totalling at least 75% by weight, and with a content of lipids, emulsifiers and lipophilic constituents totalling at least 15%, based in each case on the total weight of the preparations,
(c) the oil phase of which comprises at least 75% of one or more substances chosen from the group of nonpolar lipids which are liquid at room temperature and have a polarity of greater than 30 mN/m, and/or silicones of any polarity this weight proportion being based on the total weight of the oil phase,
(d) comprising at least one interface-active substance chosen from the group of substances of the general formula (I)

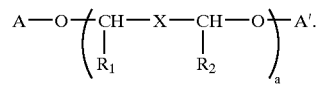

10 Claims, No Drawings

FLOWABLE PREPARATIONS OF THE WATER-IN-OIL EMULSION TYPE HAVING AN INCREASED WATER CONTENT

This is application is a 371 of PCT/99/05816, which was filed Jun. 16, 1999.

The present invention relates to cosmetic and dermatological preparations, in particular those of the water-in-oil type, to processes for their preparation and to their use for cosmetic and medicinal purposes.

The human skin is man's largest organ and performs a number of vital functions. Having an average area of about 2 m² in adults, it has a prominent role as a protective and sensory organ. The purpose of this organ is to transmit and avert mechanical, thermal, actinic, chemical and biological stimuli. In addition, it has an important role as a regulatory and target organ in human metabolism.

The main aim of skin care in the cosmetics sense is to strengthen or rebuild the skin's natural function as a barrier against environmental influences (e.g. dirt, chemicals, microorganisms) and against the loss of endogenous substances (e.g. water, natural fats, electrolytes), and also to assist its horny layer in its natural regeneration ability where damage has occurred.

If the barrier properties of the skin are impaired, increased resorption of toxic or allergenic substances or infection by microorganisms may result, leading to toxic or allergic skin reactions.

Another aim of skin care is to compensate for the loss by the skin of sebum and water caused by daily washing. This is particularly important if the natural regeneration ability is inadequate. Furthermore, skin care products should protect against environmental influences, in particular against sun and wind, and delay skin ageing.

Medicinal topical compositions usually comprise one or more medicaments in an effective concentration. For the sake of simplicity, in order to clearly distinguish between cosmetic and medicinal use and corresponding products, reference is made to the legal provisions in the Federal Republic of Germany (e.g. Cosmetics Directive, Foods and Drugs Act).

Emulsions are generally taken to mean heterogeneous systems which consist of two liquids which are immiscible or miscible with one another only to a limited extent, which are usually referred to as phases. In an emulsion, one of the two liquids is dispersed in the form of very fine droplets in the other liquid.

If the two liquids are water and oil and oil droplets are very finely dispersed in water, this is an oil-in-water emulsion (O/W emulsion, e.g. milk). The basic character of an O/W emulsion is determined by the water. In the case of a water-in-oil emulsion (W/O emulsion, e.g. butter), the principle is reversed, the basic structure being determined here by the oil.

The person skilled in the art is of course aware of a large number of ways to formulate stable W/O preparations for cosmetic or dermatological use, for example in the form of creams and ointments which can be spread in the range from room temperature to skin temperature, or as lotions and milks, which are more likely flowable in this temperature range. However, there are only a few formulations in the prior art which are of sufficiently low-viscosity that they would, for example, be sprayable.

In addition, low-viscosity preparations of the prior art frequently have the disadvantage that they are unstable, and are limited to a narrow field of application or a limited choice of feed materials. Low-viscosity products in which, for example, strongly polar oils—such as the plant oils otherwise frequently used in commercially available products—are sufficiently stabilized are therefore currently not on the market.

W/O emulsions with a high water content and a low viscosity which moreover have storage stability, as is required for marketable products, can only be formulated in accordance with the prior art in a very complex manner. Accordingly, the supply of formulations of this type is extremely low. Nevertheless, formulations of this type could offer the consumer hitherto unknown cosmetic performances.

An object of the present invention was to provide preparations which have a very low viscosity and do not have the disadvantages of the prior art.

Another object of the present invention was to provide preparations which can be charged with a high content of water-soluble and/or water-miscible substances having cosmetic or dermatological activity, without impairing the galenical quality or other properties of the preparations.

According to K. J. Lissant: The *Geometry of High-Internal-Phase-Ratio Emulsions*; Journal of Colloid and Interface Science 22, 462–468 (1966), emulsions with an internal phase of more than 70% are defined as so-called high internal phase emulsions. The preparation of stable, flowable water-in-oil emulsions with a water content of more than 70% is very difficult. In particular, "high internal phase" W/O emulsions with a very high water content of more than 85% ("very high internal phase" W/O emulsions) are not accessible.

The technique of varying the phase volume ratio (i.e. incorporating higher amounts of liquid lipids) which is usually used for water-in-oil emulsions can, because of the low lipid content, be used only to a limited extent in the case of high internal phase W/O emulsions, or not at all in the case of very high internal phase W/O emulsions. Therefore, only water-in-oil emulsions with a solid to semisolid consistency are obtainable. Even the use of polar lipids, by virtue of which lower-viscosity water-in-oil emulsions are usually obtained, does not lead to the desired success.

Surprisingly, it has been found that water-in-oil emulsions (a) with a viscosity of at most 5000 mPa.s (b) with a content of water and optionally water-soluble substances totalling at least 75% by weight, and with a content of lipids, emulsifiers and lipophilic constituents totalling at least 15%, based in each case on the total weight of the preparations, (c) the oil phase of which comprises at least 75% of one or more substances chosen from the groups of
nonpolar lipids which are liquid at room temperature and have a polarity of greater than 30 mN/m, and/or silicones of any polarity this weight proportion being based on the total weight of the oil phase, (d) comprising at least one interface-active substance chosen from the group of substances of the general formula (I)

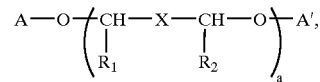

where A and A' are identical or different organic radicals chosen from the group of branched and unbranched, saturated and unsaturated alkyl and acyl radicals and hydroxyacyl radicals having 10–30 carbon atoms, and also from the group of hydroxyacyl groups connected to one another via ester functions, in accordance with the scheme

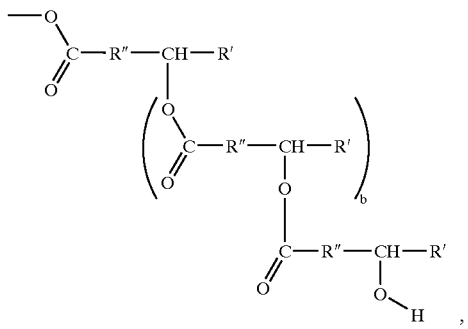

where R' is chosen from the group of branched and unbranched alkyl groups having 1 to 20 carbon atoms and R" is chosen from the group of branched and unbranched alkylene groups having 1 to 20 carbon atoms, and b can assume numbers from 0 to 200, a is a number from 1 to 100, preferably 2 to 60, in particular 5 to 40, X is a single bond or the group

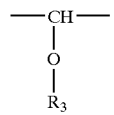

$R_1$ and $R_2$ independently of one another are chosen from the group consisting of H and methyl, $R_3$ is chosen from the group consisting of H, and the branched and unbranched, saturated and unsaturated alkyl and acyl radicals having 1 to 20 carbon atoms overcome the disadvantages of the prior art.

The structural formula must not be interpreted as meaning that because of the index a, all of the radicals $R_1$, $R_2$ and $R_3$ represented in the brackets must in each case be identical throughout the entire molecule. Instead, these radicals can be freely chosen in each of the a fragments

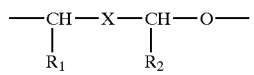

It is possible and advantageous to choose the total content of water and water-soluble substances of the W/O emulsions according to the invention to be greater than 80% by weight, in particular 85% by weight, in each case based on the total weight of the preparations.

An example of interface-active substances which can be used particularly advantageously for the purposes of the present invention is polyethylene glycol-30 dipolyhydroxystearate (PEG-30 dipolyhydroxystearate), which is sold by ICI Surfactants under the trade name ARLACEL® P135.

The total amount of interface-active substances used according to the invention in the finished cosmetic or dermatological preparations is advantageously chosen from the range 0.1–30% by weight, preferably 0.25–5.0% by weight, in particular 0.75–3.5% by weight, based on the total weight of the preparations.

Although it is known that W/O emulsions with a high water content can be produced using emulsifiers of the type described previously, the known prior art was nevertheless unable to indicate the route to the present invention.

For the purposes of the present disclosure, a general term for fats, oils, waxes and the like which is sometimes used is the term "lipids", with which the person skilled in the art is entirely familiar. The terms "oil phase" and "lipid phase" are also used synonymously.

Oils and fats differ from one another in their polarity, which is difficult to define. It has already been proposed to adopt the interfacial tension towards water as a measure of the polarity index of an oil or of an oil phase. This means that the lower the interfacial tension between this oil phase and water, the greater the polarity of the oil phase in question. According to the invention, the interfacial tension is regarded as one possible measure of the polarity of a given oil component.

The interfacial tension is the force which acts on an imaginary line one metre in length in the interface between two phases. The physical unit for this interfacial tension is conventionally calculated from the force/length relationship and is usually expressed in mN/m (millinewtons divided by metres). It has a positive sign if it endeavours to reduce the interface. In the converse case, it has a negative sign.

The limit below which an oil phase is "polar" and above which an oil phase is "nonpolar" is regarded as 30 mN/m according to the invention.

The following nonpolar lipids which are liquid at room temperature have proven particularly advantageous: hydrocarbons (mineral oils, cycloparaffin, polyisobutenes, polydecenes), nonethoxylated or nonpropoxylated ethers (caprylyl ether/Cetiol OE) and silicone oils (dimethicone, cyclomethicone, dimethiconol).

According to the above definition of polarity, silicone oils are not nonpolar, but usually fall in the mid-polar region (typically between 20 and 30 mN/m).

According to the invention, it is possible to tolerate a certain proportion of polar lipids in the lipid mixture, although this proportion should on no account exceed 25% by weight, is preferably less than 15% by weight and should in an ideal case be no more than ≦10% by weight, based on the total lipid phase.

According to the teaching presented herewith, W/O emulsions are obtainable whose viscosity at 25° C. is less than 5000 mPa.s (=millipascal seconds), in particular less than 4000 mPa.s, preferably less than 3500 mPas (HAAKE Viscotester VT-02).

Advantageously, the oils according to the invention are likewise chosen from the group of paraffin oils, polyolefins and Vaseline (petrolatum). Of the polyolefins, polydecenes and hydrogenated polyisobutene are the preferred substances.

For the purposes of the present invention, the oil phase can additionally—provided the features listed in the patent claims are considered—advantageously comprise substances chosen from the group of esters of saturated and/or unsaturated, branched and/or unbranched alkanecarboxylic acids having a chain length of from 3 to 30 carbon atoms and saturated and/or unsaturated, branched and/or unbranched alcohols having a chain length of from 3 to 30 carbon atoms and from the group of esters of aromatic carboxylic acids and saturated and/or unsaturated, branched and/or unbranched alcohols having a chain length of from 3 to 30 carbon atoms. Such ester oils can then advantageously be chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and also synthetic, semisynthetic and natural mixtures of such esters, such as, for example, jojoba oil.

The oil phase can also be chosen advantageously from the group of branched and unbranched hydrocarbons and hydrocarbon waxes, silicone oils, dialkyl ethers, the group of saturated or unsaturated, branched or unbranched alcohols, and fatty acid triglycerides, namely the triglycerol esters of saturated and/or unsaturated, branched and/or unbranched alkanecarboxylic acids having a chain length of from 8 to 24 carbon atoms, in particular 12–18 carbon atoms. The fatty acid triglycerides can, for example, be advantageously chosen from the group of synthetic, semisynthetic and natural oils, e.g. olive oil, sunflower oil, soya oil, peanut oil, rapeseed oil, almond oil, palm oil, coconut oil, palm kernel oil and the like.

If desired, fatty and/or wax components which are to be used in the oil phase—as secondary constituents in a minor amount—can be chosen from the group of vegetable waxes, animal waxes, mineral waxes and petrochemical waxes. Examples which are favourable according to the invention are candelilla wax, carnauba wax, japan wax, esparto grass wax, cork wax, guaruma wax, rice germ oil wax, sugarcane wax, berry wax, ouricury wax, montan wax, jojoba wax, shea butter, beeswax, shellac wax, spermaceti, lanolin (wool wax), uropygial grease, ceresin, ozocerite (earth wax), paraffin waxes and microcrystalline waxes.

Other advantageous fatty and/or wax components are chemically modified waxes and synthetic waxes such as, for example, those obtainable under the trade names Syncrowax HRC (glyceryl tribehenate), Syncrowax HGLC ($C_{16-36}$-fatty acid triglyceride) and Syncrowax AW 1C ($C_{18-36}$-fatty acid) from CRODA GmbH, and also montan ester waxes, Sasol waxes, hydrogenated jojoba waxes, synthetic or modified beeswaxes (e.g. dimethicone copolyol beeswax and/or $C_{30-50}$-alkyl beeswax), polyalkylene waxes, polyethylene glycol waxes, but also chemically modified fats, such as, for example, hydrogenated vegetable oils (for example hydrogenated castor oil and/or hydrogenated coconut fatty glycerides), triglycerides, such as, for example, trihydroxystearin, fatty acids, fatty acid esters and glycol esters, such as, for example, $C_{20-40}$-alkyl stearate, $C_{20-40}$-alkylhydroxystearoyl stearate and/or glycol montanate. Also advantageous are certain organosilicon compounds, which have similar physical properties to the specified fatty and/or wax components, such as, for example, stearoxytrimethylsilane.

If desired, the fatty and/or wax components can be present either individually or as a mixture.

Any desired mixtures of such oil and wax components can also be used to advantageously for the purposes of the present invention. In some instances, it can also be advantageous to use waxes, for example cetyl palmitate, as the lipid component of the oil phase.

Of the hydrocarbons, paraffin oil, hydrogenated polyolefins (e.g. hydrogenated polyisobutene), squalane and squalene can be used advantageously for the purposes of the present invention.

According to the invention, emulsions which are particularly advantageous are those which are characterized in that the oil phase consists of at least 50% by weight, preferably of more than 75% by weight, of at least one substance chosen from the group consisting of vaseline (petrolatum), paraffin oil and polyolefins, and of the latter, preference is given to polydecenes.

The oil phase can advantageously additionally have a content of cyclic or linear silicone oils or consist entirely of such oils, although it is preferable to use an additional content of other oil phase components apart from the silicone oil or the silicone oils.

Cyclomethicone (octamethylcyclotetrasiloxane) can be used advantageously. However, other silicone oils can also be used advantageously for the purposes of the present invention, for example hexamethylcyclotrisiloxane, polydimethylsiloxane and poly(methylphenylsiloxane).

The aqueous phase of the preparations according to the invention in some instances advantageously comprises alcohols, diols or polyols of low carbon number, and ethers thereof, preferably ethanol, isopropanol, propylene glycol, glycerol, ethylene glycol, ethylene glycol monoethyl ether or monobutyl ether, propylene glycol monomethyl, monoethyl or monobutyl ethers, diethylene glycol monomethyl or monoethyl ethers and analogous products, and also alcohols of low carbon number, e.g. ethanol, isopropanol, 1,2-propanediol and glycerol and in particular one or more thickeners which can advantageously be chosen from the group silicon dioxide, aluminium silicates, polysaccharides and derivatives thereof, e.g. hyaluronic acid, xanthan gum, hydroxypropylmethylcellulose, particularly advantageously from the group of polyacrylates, preferably a polyacrylate from the group of so-called Carbopols, for example Carbopol grades 980, 981, 1382, 2984, 5984, or also ETD (easy-to-disperse) grades 2001, 2020, 2050, in each case individually or in any combinations with one another.

A particular advantage of the present invention is that it permits high concentrations of polyols, in particular glycerol, to be used.

Particularly advantageous preparations are also obtained when antioxidants are used as additives or active ingredients. According to the invention, the preparations advantageously comprise one or more antioxidants. Antioxidants which are favourable but which are nevertheless optional may be all antioxidants which are customary or suitable for cosmetic and/or dermatological application.

The antioxidants are advantageously selected from the group consisting of amino acids (e.g. glycine, histidine, tyrosine, tryptophan) and their derivatives, imidazoles, (e.g. urocanic acid) and their derivatives, peptides, such as D,L-carnosine, D-carnosine, L-carnosine and their derivatives (e.g. anserine), carotenoids, carotenes (e.g. α-carotene, β-carotene, ψ-lycopene) and their derivatives, lipoic acid and its derivatives (e.g. dihydrolipoic acid), aurothioglucose, propylthiouracil and other thiols (e.g. thioredoxin, glutathione, cysteine, cystine, cystamine and their glycosyl, N-acetyl, methyl, ethyl, propyl, amyl, butyl and lauryl, palmitoyl, oleyl, γ-linoleyl, cholesteryl and glyceryl esters) and their salts, dilauryl thiodipropionate, distearyl thiodipropionate, thiodipropionic acid and its derivatives (esters, ethers, peptides, lipids, nucleotides, nucleosides and salts) and sulphoximine compounds (e.g. buthionine sulphoximines, homocysteine sulphoximine, buthionine sulphones, penta-, hexa-, heptathionine sulphoximines) in very low tolerated doses (e.g. pmol to µmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and their derivatives, unsaturated fatty acids and their derivatives (e.g. γ-linolenic acid, linoleic acid, oleic acid), folic acid and its derivatives, ubiquinone and ubiquinol and their derivatives, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of benzoin resin, rutinic acid and its derivatives, ferulic acid and its derivatives, butylated hydroxytoluene, butylated hydroxyanisole, nordihydroguaiacic acid, nordihydroguaiareticic acid, trihydroxybutyrophenone, uric acid and its derivatives, mannose and its derivatives, zinc and its derivatives (e.g. ZnO, $ZnSO_4$), selenium and its derivatives (e.g. selenomethionine), stilbenes and their derivatives (e.g. stilbene oxide, trans-stilbene oxide), and the derivatives (salts, esters, ethers, sugars, nucleotides, nucleosides, peptides and lipids) of said active substances which are suitable according to the invention.

For the purposes of the present invention, oil-soluble antioxidants can be used particularly advantageously.

A surprising property of the present invention is that preparations according to the invention are very good vehicles for cosmetic or dermatological active ingredients into the skin, preferred active ingredients being antioxidants which are able to protect the skin against oxidative stress. Preferred antioxidants are vitamin E and its derivatives and vitamin A and its derivatives.

The amount of antioxidants (one or more compounds) in the preparations is preferably from 0.001 to 30% by weight, particularly preferably 0.05–20% by weight, in particular 1–10% by weight, based on the total weight of the preparation.

If vitamin E and/or its derivatives are used as the antioxidant or antioxidants, their respective concentrations are advantageously chosen from the range of 0.001–10% by weight, based on the total weight of the formulation.

If vitamin A or vitamin A derivatives or carotenes or their derivatives are used as the antioxidant or antioxidants, their respective concentrations are advantageously chosen from the range of 0.001–10% by weight, based on the total weight of the formulation.

The person skilled in the art is of course aware that cosmetic preparations are in most cases inconceivable without the customary auxiliaries and additives. The cosmetic and dermatological preparations according to the invention can, accordingly, also comprise cosmetic auxiliaries, as are customarily used in such preparations, for example bodying agents, stabilizers, fillers, preservatives, perfumes, antifoams, dyes, pigments which have a colouring action, thickeners, surface-active substances, emulsifiers, emollients, moisturizers and/or humectants, anti-inflammatory substances, additional active ingredients such as vitamins or proteins, sunscreens, insect repellants, bactericides, virucides, water, salts, antimicrobial, proteolytic or keratolytic substances, medicaments or other customary constituents of a cosmetic or dermatological formulation such as alcohols, polyols, polymers, foam stabilizers, organic solvents or also electrolytes.

The latter can be chosen, for example, from the group of salts containing the following anions: chlorides, also inorganic oxo element anions, of these, in particular sulphates, carbonates, phosphates, borates and aluminates. Electrolytes based on organic anions are also advantageous, e.g. lactates, acetates, benzoates, propionates, tartrates, citrates, amino acids, ethylenediaminetetraacetic acid and salts thereof and others. Preferred cations of the salts are ammonium, alkylammonium, alkali metal, alkaline earth metal, magnesium, iron or zinc ions. It does not need to be mentioned that only physiologically acceptable electrolytes should be used in cosmetics. Particular preference is given to potassium chloride, sodium chloride, magnesium sulphate, zinc sulphate and mixtures thereof.

Corresponding requirements apply mutatis mutandis to the formulation of medicinal preparations.

The W/O emulsions according to the invention can be used as a basis for cosmetic or dermatological formulations. The latter can have the customary composition and be used, for example, for the treatment and care of the skin and/or the hair, as lip care product, as deodorant product and as make-up or make-up remover product in decorative cosmetics or as a sunscreen preparation. For use, the cosmetic and dermatological preparations according to the invention are applied to the skin and/or the hair in a sufficient amount in a manner customary for cosmetics or dermatological compositions.

For the purposes of the present invention, cosmetic or topical dermatological compositions can accordingly, depending on their composition, be used, for example, as a skin protection cream, cleansing milk, sunscreen lotion, nourishing cream, day or night cream, etc. In some circumstances it is possible and advantageous to use the compositions according to the invention as a base for pharmaceutical formulations.

The low-viscosity cosmetic or dermatological compositions according to the invention can, for example, be in the form of preparations which can be sprayed from aerosol containers, squeezable bottles or by means of a pump device, or in the form of a liquid composition which can be applied by means of roll-on devices, but also in the form of an emulsion which can be applied from normal bottles and containers.

Suitable propellants for cosmetic or dermatological preparations which can be sprayed from aerosol containers for the purposes of the present invention are the customary known readily volatile, liquefied propellants, for example hydrocarbons (propane, butane, isobutane), which can be used alone or in a mixture with one another. Compressed air is also used advantageously.

The person skilled in the art is of course aware that there are propellants which are non-toxic per se which would be suitable in principle for realizing the present invention in the form of aerosol preparations, but which must nevertheless be avoided because of their unacceptable impact on the environment or other accompanying circumstances, in particular fluorinated hydrocarbons and chlorofluorocarbons (CFCs).

Cosmetic and dermatological preparations which are in the form of a sunscreen are also favourable. As well as the active ingredient combinations according to the invention, these preferably additionally comprise at least one UV-A filter substance and/or at least one UV-B filter substance and/or at least one inorganic pigment.

For the purposes of the present invention, however, it is also advantageous to provide cosmetic and dermatological preparations whose main purpose is not protection against sunlight, but which nevertheless have a content of UV protectants. Thus, for example, UV-A or UV-B filter substances are usually incorporated into day creams.

UV protectants, like antioxidants and, if desired, preservatives, also effectively protect the preparations themselves against decay.

Preparations according to the invention can advantageously comprise further substances. which absorb UV radiation in the UV-B range, the total amount of filter substances being, for example, from 0.1% by weight to 30% by weight, preferably from 0.5 to 10% by weight, in particular from 1.0 to 6.0% by weight, based on the total weight of the preparations, in order to provide cosmetic preparations which protect the hair and/or the skin from the whole region of ultraviolet radiation. They can also be used as sunscreens for the hair or the skin.

If the emulsions according to the invention contain UV-B filter substances, the latter may be oil-soluble or water-soluble. Examples of oil-soluble UV-B filters which are advantageous according to the invention are:

3-benzylidenecamphor derivatives, preferably 3(4-methylbenzylidene)-camphor, 3-benzylidenecamphor;
4-aminobenzoic acid derivatives, preferably 2-ethylhexyl 4-(dimethylamino)benzoate, amyl 4-(dimethylamino) benzoate;
esters of cinnamic acid, preferably 2-ethylhexyl 4-methoxycinnamate, isopentyl 4-methoxycinnamate;
esters of salicylic acid, preferably 2-ethylhexyl salicylate, 4-isopropylbenzyl salicylate, homomenthyl salicylate;
derivatives of benzophenone, preferably 2-hydroxy-4-methoxybenzophenone, 2-hydroxy-4-methoxy-4'-methylbenzophenone, 2,2'-di-hydroxy-4-methoxybenzophenone;
esters of benzalmalonic acid, preferably di(2-ethylhexyl) 4-methoxybenzalmalonate;
derivatives of 1,3,5-triazine, preferably 2,4,6-trianilino(p-carbo-2'-ethyl-1'-hexyloxy)-1,3,5-triazine.

The list of said UV-B filters, which may be used in combination with the active ingredient combinations according to the invention is of course not intended to be limiting.

It can also be advantageous to formulate lipodispersions according to the invention with UV-A filters which have hitherto been customarily present in cosmetic preparations. These substances are preferably derivatives of dibenzoylmethane, in particular 1-(4'-tert-butylphenyl)-3-(4'-methoxyphenyl)-propane-1,3-dione and 1-phenyl-3-(4'-isopropylphenyl)propane-1,3-dione.

Cosmetic and dermatological preparations according to the invention can also comprise inorganic pigments which are customarily used in cosmetics for protecting the skin against UV rays. These are oxides of titanium, zinc, iron, zirconium, silicon, manganese, aluminium, cerium and mixtures thereof, and modifications in which the oxides are the active agents. Particular preference is given to pigments based on titanium dioxide.

Further constituents which can be used are:
fats, waxes and other natural and synthetic fatty substances, preferably esters of fatty acids with alcohols of low carbon number, e.g. with isopropanol, propylene glycol or glycerol, or esters of fatty alcohols with alkanoic acids of low carbon number or with fatty acids;
alcohols, diols or polyols of low carbon number, and their ethers, preferably ethanol, isopropanol, propylene glycol, glycerol, ethylene glycol, ethylene glycol monoethyl or monobutyl ethers, propylene glycol monomethyl, monoethyl or monobutyl ethers, diethylene glycol monomethyl or monoethyl ethers and analogous products.

Preparations according to the invention can also comprise active ingredients (one or more compounds) which are chosen from the group: acetylsalicylic acid, atropine, azulene, hydrocortisone and derivatives thereof, e.g. hydrocortisone-17 valerate, vitamins, e.g. ascorbic acid and derivatives thereof, vitamins of the B and D series, very favourably vitamin $B_1$, vitamin $B_{12}$ and vitamin $D_1$, but also bisabolol, unsaturated fatty acids, namely the essential fatty acids (often also called vitamin F), in particular γ-linolenic acid, oleic acid, eicosapentanoic acid, docosahexanoic acid and derivatives thereof, chloramphenicol, caffeine, prostaglandins, thymol, camphor, extracts or other products of a vegetable and animal origin, e.g. evening primrose oil, star flower oil or currant seed oil fish oils, cod-liver oil or also ceramides or ceramide-like compounds etc. It is also advantageous to choose the active ingredients from the group of refatting substances, for example purcellin oil, Eucerit® and Neocerit®.

The amount of such active ingredients (one or more compounds) in the preparations according to the invention is preferably from 0.001 to 30% by weight, particularly preferably 0.05–20% by weight, in particular 1–10% by weight, based on the total weight of the preparation.

The examples below serve to illustrate the present invention without limiting it. The numerical values in the examples refer to percentages by weight, based on the total weight of the respective preparations.

EXAMPLE 1
(W/O Lotion)

|  | % by weight |
|---|---|
| PEG-30 Dipolyhydroxystearate | 2.00 |
| Isohexadecane | 4.50 |
| Paraffinum liquidum | 12.50 |
| Glycerol | 3.00 |
| Magnesium sulphate | 0.70 |
| Perfume, preservatives, dyes, antioxidants | q.s. |
| Water | ad. 100.0 |

EXAMPLE 2
(W/O Lotion)

|  | % by weight |
|---|---|
| PEG-30 Dipolyhydroxystearate | 2.00 |
| Squalane | 6.00 |
| Paraffinum liquidum | 6.00 |
| Hydrogenated polyisobutene | 6.00 |
| Glycerol | 3.00 |
| Magnesium sulphate | 0.70 |
| Perfume, preservatives, dyes, antioxidants | q.s. |
| Water | ad. 100.0 |

EXAMPLE 3
(W/O Lotion)

|  | % by weight |
|---|---|
| PEG-30 Dipolyhydroxystearate | 2.00 |
| Cycloparaffin | 10.00 |
| Paraffinum liquidum | 7.50 |
| Tocopherol acetate | 0.50 |
| Glycerol | 3.00 |
| Panthenol | 0.30 |
| 1,3-Butylene glycol | 1.00 |
| Serine | 0.30 |
| Biotin | 0.10 |
| Distarch phosphate | 1.00 |
| Magnesium sulphate | 0.70 |
| Perfume, preservatives, dyes, antioxidants | q.s. |
| Water | ad. 100.0 |

EXAMPLE 4
(W/O Lotion)

| | % by weight |
|---|---|
| PEG-30 Dipolyhydroxystearate | 2.00 |
| Isohexadecane | 4.00 |
| Paraffinum subliquidum | 8.00 |
| 4-(tert-Butyl)-4'-methoxydibenzoylmethane | 1.00 |
| Octyl methoxycinnamate | 1.50 |
| 4-Methylbenzylidenecamphor | 1.50 |
| Tris[anilino(p-carbo-2'-ethyl-1'-hexyloxy)]triazine | 0.50 |
| Titanium dioxide | 1.00 |
| Zinc oxide | 1.00 |
| Glycerol | 1.00 |
| Magnesium sulphate | 0.70 |
| Perfume, preservatives, dyes, antioxidants | q.s. |
| Water | ad. 100.0 |

EXAMPLE 5
(W/O Lotion)

| | % by weight |
|---|---|
| PEG-30 Dipolyhydroxystearate | 2.00 |
| Isohexadecane | 5.00 |
| Paraffinum liquidum | 10.00 |
| Glycerol | 3.00 |
| Sodium chloride | 0.70 |
| Perfume, preservatives, dyes, antioxidants | q.s. |
| Water | ad. 100.0 |

EXAMPLE 6
(Liquid Emulsion Make-up)

| | % by weight |
|---|---|
| PEG-30 Dipolyhydroxystearate | 2.00 |
| Isohexadecane | 3.00 |
| Paraffinum liquidum | 13.00 |
| Glycerol | 1.50 |
| Magnesium silicate | 0.50 |
| Mica | 0.50 |
| Iron oxides | 0.50 |
| Titanium dioxide | 0.50 |
| Talc | 0.50 |
| Magnesium sulphate | 0.70 |
| Perfume, preservatives, dyes, antioxidants | q.s. |
| Water | ad. 100.0 |

EXAMPLE 7
(W/O Lotion)

| | % by weight |
|---|---|
| PEG-30 Dipolyhydroxystearate | 2.50 |
| Squalane | 3.00 |
| Polydecene | 3.00 |
| Paraffinum liquidum | 7.00 |
| Hydrogenated polyisobutene | 1.00 |
| Glycerol | 1.00 |
| Sorbitol | 5.00 |
| Magnesium sulphate | 0.70 |
| Perfume, preservatives, dyes, antioxidants | q.s. |
| Water | ad. 100.0 |

EXAMPLE 8
(W/O Lotion)

| | % by weight |
|---|---|
| PEG-30 Dipolyhydroxystearate | 2.0 |
| Isohexadecane | 5.00 |
| Paraffinum liquidum | 5.00 |
| Glycerol | 20.0 |
| Magnesium sulphate | 0.70 |
| Perfume, preservatives, dyes, antioxidants | q.s |
| Water | ad. 100.0 |

What is claimed is:

1. A water-in-oil (W/O) emulsion having a viscosity of at most 5000 mPa.s, said W/O emulsion comprising:

a) an aqueous phase comprising a content of water and water-soluble substances totaling at least 75% by weight, based on a total weight of the emulsion:

b) an oil phase comprising a content of lipids, emulsifiers and lipophilic constituents totaling at least 15% by weight, based on a total weight of the emulsion, wherein the oil phase comprises at least 75% by weight, based on the weight of the oil phase, of one or more substances selected from the group consisting of:

i) non-polar lipids which are liquid at room temperature and have a polarity of greater than 30 mN/m; and ii) silicones of any polarity;

c) at least one interface-active substance selected from the group consisting of substances of the formula (I);

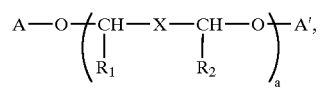

where A and A' are identical or different organic radicals selected from the group consisting of branched and unbranched, saturated and unsaturated alkyl and acyl radicals and hydroxyacyl radicals having 10–30 carbon atoms, and also from the group consisting of hydroxyacyl groups connected to one another via ester functions in accordance with the following scheme:

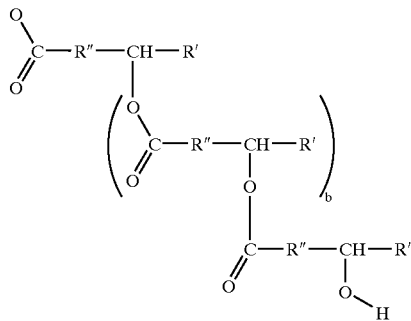

where R' is selected from the group consisting of branched and unbranched alkyl groups having 1 to 20 carbon atoms and R" is selected from the group consisting of branched and unbranched alkylene groups having 1 to 20 carbon atoms, and b is a number from 0 to 200;

a is a number from 1 to 100:

X is a single bond or the group:

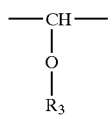

$R_1$ and $R_2$ independently represent H or methyl; and $R^3$ is selected from the group consisting of H and branched and unbranched, saturated and unsaturated alkyl and acyl radicals having 1 to 20 carbon atoms.

2. The W/O emulsion according to claim 1, wherein a is a number from 2 to 60.

3. The W/O emulsion according to claim 2, wherein a is a number from 5 to 40.

4. The W/O emulsion according to claim 1, wherein the content of water and water soluble substances is greater than 80% by weight, based on the total weight of the emulsion.

5. The W/O emulsion according to claim 4, wherein the content of water and water soluble substances is greater than 85% by weight, based on the total weight of the emulsion.

6. The W/O emulsion according to claim 1, wherein the interface-active substance is polyethylene glycol-30-dipolyhydroxystearate.

7. The W/O emulsion according to claim 1, wherein the oil phase comprises at least 50% by weight, based on the total weight of the oil phase, of at least one substance selected from the group consisting of Vaseline (petrolatum), paraffin oil and polyolefins.

8. The W/O emulsion according to claim 7, wherein the oil phase comprises more than 75% by weight, based on the total weight of the oil phase, of at least one substance selected from the group consisting of Vaseline (petrolatum), paraffin oil and polyolefins.

9. The W/O emulsion according to claim 7, wherein the oil phase comprises one or more polydecenes.

10. A method of caring for skin or hair comprising topically applying thereto an effective amount therefor of the W/O emulsion according to any one of claims 1–9.

* * * * *

UNITED STATES PATENT AND TRADEMARK OFFICE
CERTIFICATE OF CORRECTION

PATENT NO. : 6,821,934 B1  Page 1 of 1
APPLICATION NO. : 09/719670
DATED : November 23, 2004
INVENTOR(S) : Bleckmann et al.

It is certified that error appears in the above-identified patent and that said Letters Patent is hereby corrected as shown below:

Column 8,
Line 61, "further substances. which absorb" should read -- further substances which absorb --.

Column 9,
Lines 8-9, "3(4-methylbenzylidene)" should read -- 3-(4-methylbenzylidene) --.

Column 10,
Line 5, "currant seed oil fish oils" should read -- currant seed oil, fish oils --.

Column 12,
Line 54, "formula (I);" should read -- formula (I): --.

Column 14,
Line 2, "$R^3$" should read -- $R_3$ --.

Signed and Sealed this

Eleventh Day of July, 2006

JON W. DUDAS
*Director of the United States Patent and Trademark Office*